United States Patent [19]

Cantoro

[11] Patent Number: 5,871,772
[45] Date of Patent: Feb. 16, 1999

[54] SODIUM HYALURONATE VISCOUS SOLUTIONS FOR USE AS MASKING FLUID IN THERAPEUTIC PHOTOKERATECTOMY BY MEANS OF EXCIMER LASER

[75] Inventor: Amalio Cantoro, Bologna, Italy

[73] Assignee: Chemedica S.A., Vouvry, Switzerland

[21] Appl. No.: 570,097

[22] Filed: Dec. 11, 1995

[30] Foreign Application Priority Data

Dec. 9, 1994 [IT] Italy ................................. RM94A0797

[51] Int. Cl.$^6$ ................................................. A61K 31/715
[52] U.S. Cl. ........................ 424/427; 514/23; 424/78.04; 604/294; 262/271; 536/55.1; 435/101
[58] Field of Search ........................ 514/23; 424/78.04; 604/294; 262/271; 536/55.1; 435/101

[56] References Cited

U.S. PATENT DOCUMENTS

| | | | |
|---|---|---|---|
| 4,141,973 | 2/1979 | Balzas et al. | 424/180 |
| 4,517,295 | 5/1985 | Bracke et al. | 435/101 |
| 5,093,487 | 3/1992 | Brown et al. | 536/55.1 |
| 5,106,615 | 4/1992 | Dikstein et al. | 424/78.04 |
| 5,409,904 | 4/1995 | Hecht et al. | 514/23 |

FOREIGN PATENT DOCUMENTS

| | | |
|---|---|---|
| 0228698 | 12/1986 | European Pat. Off. . |
| 0346467 | 12/1989 | European Pat. Off. . |
| 9218543 | 10/1992 | WIPO . |
| 9405216 | 3/1994 | WIPO . |

OTHER PUBLICATIONS

Fitzsimmons et al. "Acta Opthalmolgica", 69 (1991) 641–644.

Fagerholm et al. "Supplement to Refractive and Corneal Surgery", vol. 9 Mar./Apr. 1993, pp. 76–81.

Gartry et al. "British Journal of Ophthalmogy" 1991, 75, 258–269.

Kornmehl et al., "Arch Ophthalmology", vol. 109 Jun. 1991, 860–863.

Eisner "Ophthalmic Practice", vol. 10; No. 5, 1992, 2020–205.

Thompson et al. "Supplement to Refractive & Corneal Surgery", vol. 9, Mar./Apr. 1993, 581–85.

Muller–Steinwachs et al.", Investigative Ophthalmology and Visual Sciences" vol. 36, No. 4, Mar. 15, 1995, 3270–257.

Stark et al., "Ophthalmology", vol. 99, No. 5, May, 1992, 805–812.

Primary Examiner—Stephen Walsh
Assistant Examiner—Kenneth A. Sorensen
Attorney, Agent, or Firm—Abelman, Frayne & Schwab

[57] ABSTRACT

Sodium hyaluronate viscous aqueous solutions of molecular weight from 1,200,000 to 2,200,000 Daltons at concentrations from 0.10% to 0.40% by weight are proposed for use as masking fluid in therapeutic photokeratectomy by means of excimer laser (PTK), which realizes the ablation of superficial layers of corneal tissue for the elimination of unevenness and macula derived from different traumatic or pathological conditions. Preferably, the proposed solutions also contain one or more cationic species selected from the group consisting of sodium, potassium, calcium and magnesium ion and one or more anionic species selected from the group consisting of chloride, phosphate and citrate ion and, preferably, glucose. The solutions according to the invention wet the cornea and protect its areas which remain distressed after surgery, enabling the obtainment of uniform and smooth ablated surfaces. Further, they enable the execution of intraoperative corneal topographic tests.

14 Claims, 7 Drawing Sheets

SODIUM HYALURONATE VISCOUS SOLUTIONS FOR USE AS MASKING FLUID IN THERAPEUTIC PHOTOKERATECTOMY BY MEANS OF EXCIMER LASER

FIELD OF THE INVENTION

The present invention relates to sodium hyaluronate viscous solutions for use as masking fluid in therapeutic photokeratectomy by means of excimer laser. Particularly, the invention concerns the use of solutions containing sodium hyaluronate of defined molecular weight and concentration with the aim to wet and protect the cornea during the excimer laser operation for the elimination of corneal unevenness or macula, in order to obtain a smoothing effect in the photoablation.

PRIOR ART

As it is known, in the last decade the ophthalmology surgery has developed a new series of techniques based on the use of excimer laser, which enables the ablation of superficial layers of the corneal tissue exposed to radiations. For such purpose, argon-fluorine lasers are commonly used, emitting far ultraviolet light, at a wavelength of 193 nm, which allows the performance of operations with the maximal accuracy, with an excellent control on penetration depth and a minimal damaging effect on tissues adjacent to those exposed.

Contrary to other kind of lasers used in the clinical field, the excimer laser does not beam energy concentrated in a focal point, but it has a ray of large diameter, which through suitable openings is led to hit, in a series of impulses having predetermined duration, frequency and amplitude, large superficial keratic areas, with an accurate control of form and dimension of the areas exposed. The energy emitted is absorbed almost totally in a superficial layer of few micron and it determines the ablation, by evaporation, of little thicker than molecular layer of cornea at each impulse.

The excimer laser is largely used, to remodel the cornea for refractive purpose, in a technique known as refractive photokeratectomy (PRK), for the correction of different ametropias including, in particular, myopia. As it is known, myopia is a widespread optical defect due to a higher corneal curvature than the bulbus oculi length requires having as consequence that rays of light coming from the outside are refracted in such a way to converge in a focal point before they hit the retinae. The use of excimer laser permits, in this case, the ablation of superficial layers of corneal tissue of growing thickness toward the center, which results in a reduction of the corneal curvature.

More recently, the use of excimer laser was proposed for the removal, in therapy, of superficial corneal tissue, for the treatment of corneal unevenness or macula of different kind: dystrophic, degenerative, cicatricial or infective. Such kind of technique, named therapeutic photokeratectomy or PTK, was used, for example, in the treatment of recurrent corneal erosions, post-operative keratitis, corneal dystrophies such as that of Reis-Bueckler, maculae or corneal lesions due to Herpes simplex, surgery induced superficial unevenness, for example after keratoplasty or refractive corneal operation.

Differently from the case of refractive photokeratectomy, PTK was proposed to eliminate the corneal superficial unevennesses in order to smooth the profile, and therefore it implies the ablation of thicknesses of different tissues in different areas of the treated corneal surface. To avoid that, the exposition of the interested area to the laser action, causing the removal of an uniform layer of tissue at each impulse, gives as only final result the reproduction of the same superficial unevennesses at a greater depth, it is then necessary to use, in this kind of operation, a suitable fluid which, uniformly spread on the corneal surface, promotes a homogeneous removal of tissue.

In literature, such fluid is indicated with different names, all indicating the functions which it should accomplish, such as masking fluid, modulator, blocking agent. In any case, it is known that to be useful for the purpose such fluid must have suitable features of viscosity, elasticity, surface tension and bioadhesion to be rapidly and uniformly spread on the treated corneal surface, and furthermore must absorb the ultraviolet radiations at 193 nm and show a rate of ablation possibly nearer to that of the cornea, to simulate the behaviour of the corneal tissue relative to the laser action. Since the laser, at each impulse, removes an uniform thickness of tissue from all the exposed area, an uneven surface whose depressions are filled by a fluid which reacts to the photoablation similarly as the cornea, can give, at the end of the treatment, a homogeneously smoothed surface. Such criteria are disclosed, for example, in Gartry D. et al., "Excimer laser treatment of corneal surface pathology: laboratory and clinical study", Br. J. Ophthalmol., 75, 258–269, 1991.

Several products used as masking fluid in PTK were studied, the most tested were methylcellulose or hydroxypropylmethylcellulose (HPMC) viscous solutions. For example, Gartry et al. (above cited) propose the use, as masking fluid, of 1% by weight HPMC solution, which was compared to 2% HPMC solution and to polyvinyl alcohol solutions, whilst according to V. Thompson et al. (Philosophy and Technique for Excimer Laser Phototherapeutic Keratectomy, Suppl. a Refracr. Corneal Surg., 9, S81–S85, 1993) the more suitable fluid is, in most cases, a 1% by weight methylcellulose solution, whilst sometimes in some particular situations a concentration of 2% is indicated.

An experimental study regarding the performance of masking fluids with different features was disclosed by E. W. Kommehl et al., (A Comparative Study of Masking Fluids for Excimer Laser Phototherapeutic Keratectomy, Arch. Ophthalmol., 109, 860–863, June 1991). The present authors compared three different solutions with increasing viscosity: a 0.9% physiological solution, a 0.3% HPMC and dextran 0.1% aqueous solution, and a 1% sodium carboxymethylcellulose solution, and they found that the solution of middle viscosity gave corneal surface smoother and more regular.

Some publications on PTK (Fagerholm P. et al., 1993, Suppl. to Refract. Corneal Surg., Vol. 9, S76–S81; and Fitzsimmons T. D. and Fagerholm P., 1991, Acta Ophthalmologica, 69, 641–644) report the use, also as modulator fluid, of sodium hyaluronate viscous solutions, of a polysaccharide, naturally present in many tissues and fluids of both human and animals, that in aqueous solution behaves in a rheologic non-Newtonian way. Such characteristic renders it particularly suitable, at some concentration and molecular weight ranges, for use in the formulation of artificial tears, whilst for higher concentrations and molecular weights it is largely used in visco-elastic solutions for ocular surgery, for example as co-adjuvant in ocular microviscosurgery for anterior (cataract, keratoplasty, trabeculaectomy, etc.) and posterior (retinal detachment, retinopathy) segmentum of the eye. For these applications, the sodium hyaluronate is employed at relatively high concentrations (usually not less than 1% by weight) and has a relatively high molecular weight (usually 4 millions of Daltons), to give, to the resultant products, visco-elastic properties ensuring, during the surgery, the maintenance of ocular anatomic spaces (for example, the anterior chamber) avoiding the collapse or the separation of structure or ocular surgery (for example, sclerotic conjunctiva). The solutions tested in the prior art for use as masking fluid in operations with excimer laser are therefore visco-elastic solutions for ocular surgery, as for example the product commercialized with the trademark Healon$^R$, by Kabi Pharmacia, containing 1% of sodium hyaluronate with high molecular weight.

Georg Eisner, 1992, Ophthalmic Practice, Vol.10, No.5, discloses the characteristics of the Healon$^R$ solution, i.e. 4,000,000 Daltons of molecular weight and about 200 cst of viscosity.

Considering the several clinical tests of therapeutic photokeratectomy up to now reported, wherein one or the other of the masking fluids above cited were used, it is remarkable to note that the results were not of complete satisfaction, and that at the end of each work a further study in depth was suggested. In particular none of the fluids, used up to now, shows at the same time all the characteristics above cited, some of them having, for example, low bioadhesivity and therefore their distribution on the corneal surface is not uniform (as methylcellulose), others being too much viscous and therefore not rapidly spread in an uniform layer (as hyaluronate at high concentration) and practically all having a photoablation speed noticeably different from that of the corneal tissue.

Also because of the unsatisfactory performances of the known masking fluids, the results of PTK are often limited or made fruitless by the induction of post-treatment irregular astigmatism or hypermetropia, as it is reported, for example, in three out of four references above cited, and in Stark W. J. et al., Clinical Follow-up of 193-nm ArF Excimer Laser Photokeratectomy, Ophthalmol., 99, 805–812, 1992.

Moreover, it is remarkable that these unwanted effects of therapeutic photokeratectomy would be avoidable if it were possible to perform controls of the corneal topography during the operation, in such a way to exactly evaluate the effect of photoablation during the treatment and to stop it as soon as the wanted superficial evenness is obtained. Nevertheless, an intraoperative topographic control of the cornea was not realized up to now, because the masking fluids of the prior art did not enable the implementation, and the suitable time to stop the treatment was determined according to subjective impressions, evaluating visually the transparency of the cornea, without verifying the superficial evenness.

As it is known, the corneal topography is detected with devices generally known as keratoscopes, which project a series of concentric circles on the corneal surface. The evaluation of the form of the concentric aims of the reflected image from the cornea gives an indication on the conformation of the latter. Such detection can also be associated to photographic devices or video cameras, and the obtained image can be analysed by means of computer. Since none of the masking fluids used so far for PTK can be rapidly and uniformly distributed on the corneal surface on which it is dripped during the treatment, rapidly forming a film which can substitute, in order to detect by keratoscope, the corneal epithelium which was removed ahead of the treatment, an intraoperative topographic control is actually impossible and cannot be realized.

Alternatively to the modulator agents in fluid form as those so far described, some products based on collagen, which are transformed in gel in situ, after application on the cornea, so that they can form on the cornea an adherent and uniform coating, were also proposed (PCT application No. 94/05216). Such modulators in gel should have a behaviour similar to that of the corneal tissue and the same speed of photoablation, but their preparation and application are complicated (it requires, in some cases, the use of a contact lens to uniformly distribute the product), and require also the removal of remnants after treatment.

Patent applications WO-A-9218543, EP-A-0228698 and EP-A-0346467 relate to solutions of hyaluronic acid with molecular weights lower than that of Healon$^R$ for general use in ophthalmology, for example for the removal of unidentified inflammation agent, in post-operative treatment, as moistening agent and for retention of water and prevention of the bacteria invasion.

SUMMARY OF THE INVENTION

The author of the present invention has surprisingly found a masking fluid for PTK treatments showing optimal characteristics of viscosity, elasticity, surface tension and bioadhesivity to rapidly and uniformly spread on the treated corneal surface, persisting on said surface during the laser action, and, moreover, being characterized by a speed of photoablation, under the operative conditions used, as nearer as possible to that of the corneal tissue.

It has been now found that sodium hyaluronate viscous aqueous solutions can show the optimal characteristics above mentioned by a suitable choice of ranges of molecular weight and of concentration of hyaluronate, such ranges being remarkably different from those of the visco-elastic solutions, by ocular surgery based on sodium hyaluronate, up to now proposed at the experimental stage for the therapeutic photokeratectomy.

It is therefore a fundamental characteristic of the present invention the use of an aqueous solution comprising sodium hyaluronate of molecular weight from 1,200,000 to 2,200,000 Daltons in concentration comprised from 0.10% to 0.40% by weight, preferably from 1,300,000 to 2,000,000 Daltons and a concentration from 0.15% to 0.21% by weight, for the production of a masking fluid for the therapeutic photokeratectomy by means of excimer laser. Because of the non-Newton characteristics of hyaluronate, such solution has a relatively low viscosity at high values of speed of the applied shearing stress and slightly higher at low values of such speed, but on the overall the viscosity is remarkably lower than that of visco-elastic solutions like Healon$^R$, and also that of 1% HPMC solutions, being from 30 to 43 mPa.sec at 10 sec$^{-1}$.

Other advantageous properties of the proposed product are its bioadhesivity, which renders it preferable than the solutions of masking fluids based on cellulose; its elasticity, which associated to the characteristics of viscosity enables the dispersion of the amount of momentum associated to the incident laser impulse and, above all; its photoablation rate, which is much more similar to that of the corneal tissue than the photoablation rate of Healon$^R$ or 1% HPMC.

Figure 11A:
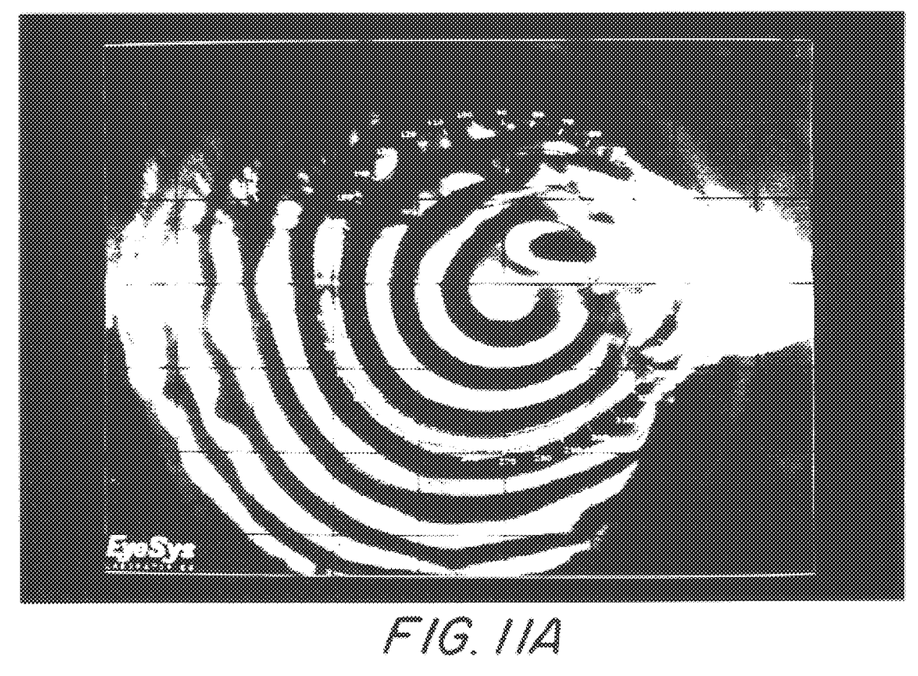
FIGS. 11A, 11B and 11C relate to topographies and show the corneal surface before the laser treatment (11A) and during treatment (11B and 11C), wherein the present solution was used.
Figure 11B:
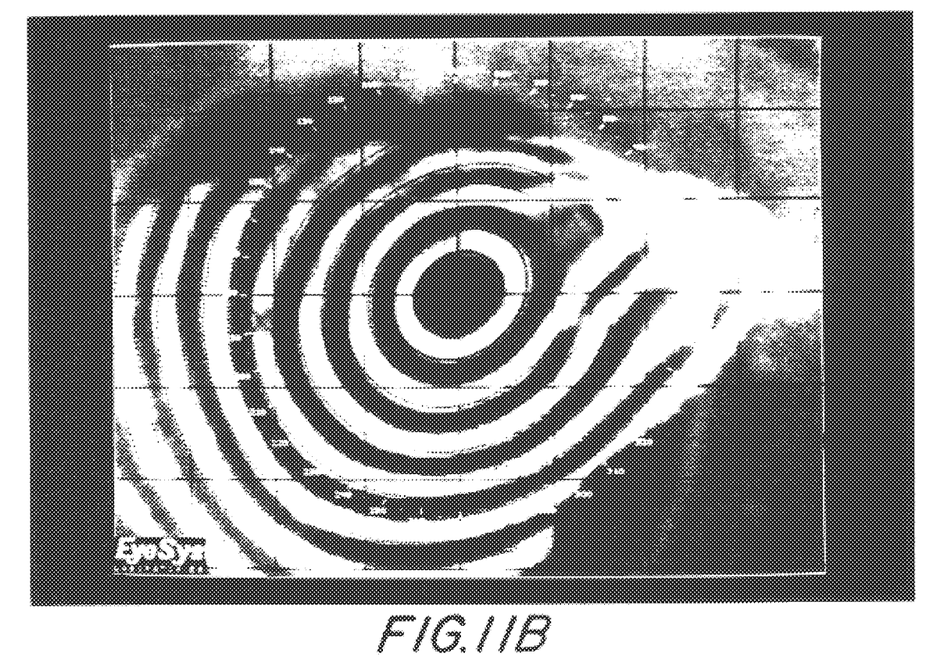
Figure 11C:
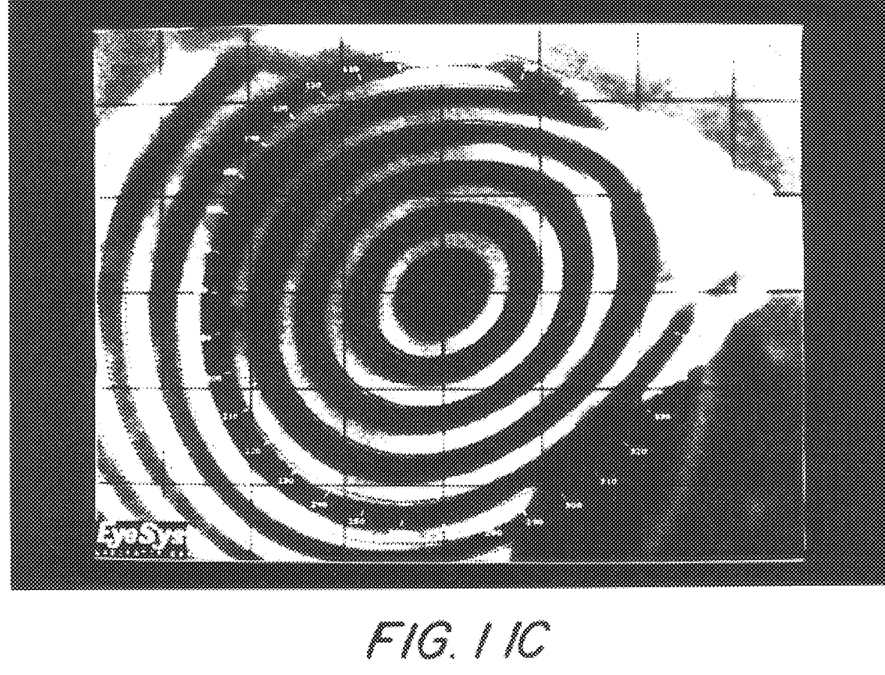

A further advantage of the present invention is that the present solution enables the performance of controls of the corneal topography during the operation, and this is of fundamental importance in order to exactly evaluate the effect of photoablation during the treatment and to stop it as soon as the wanted superficial evenness is obtained and in order to avoid damages or defects due to an incorrect subjective evaluation (see FIGS. 11A, B and C). None of the masking agents, used so far allows intraoperative topographic control.

Figure 12:
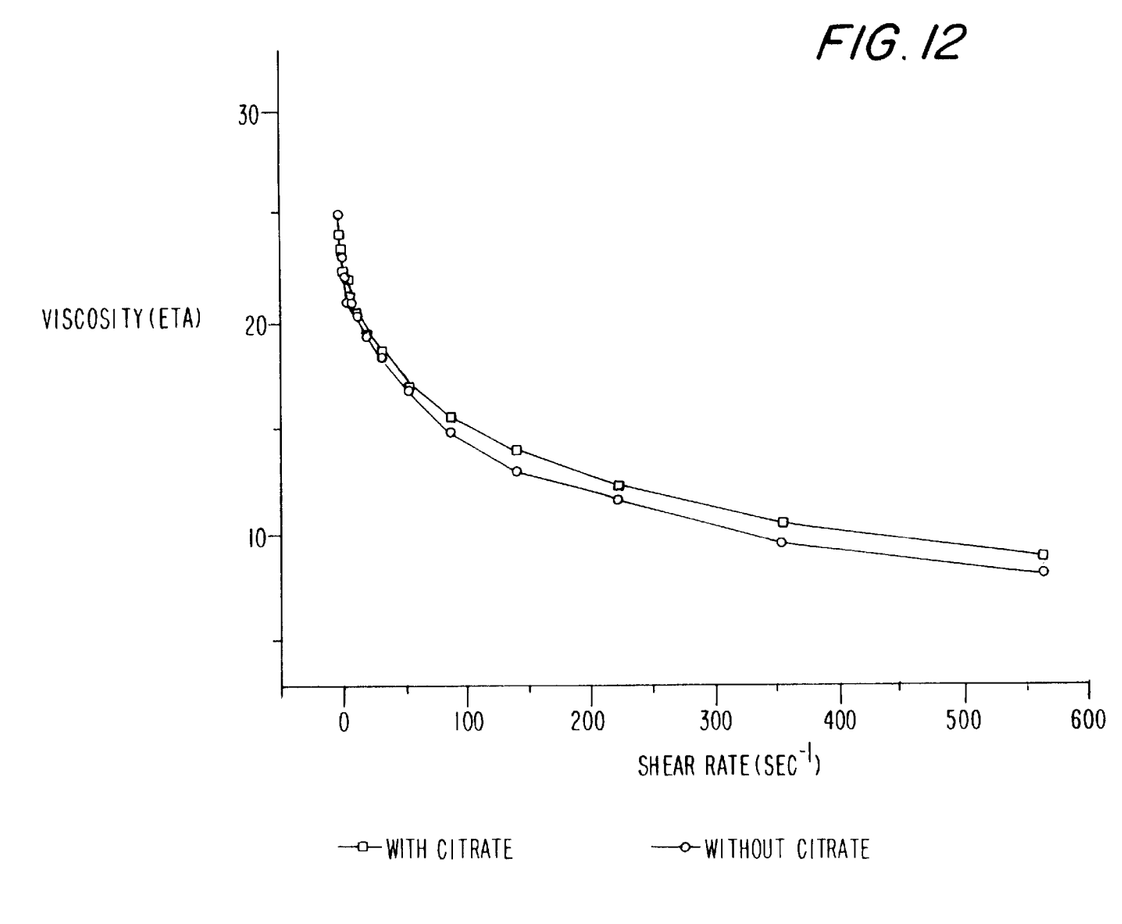
FIG. 12 is a flow curve (viscosity/shear rate) showing the viscosity behaviour of the present invention with and without citrate.

A further characteristic of the present invention refers to an aqueous solution comprising sodium hyaluronate of molecular weight from 1,200,000 to 2,200,000 Daltons in concentration comprised from 0.10% to 0.40% by weight, in combination with one or more cationic species and one or more anionic species, and in particular in combination with citrate 0.7–1.6 mmol/l (FIG. 12).

DETAILED DESCRIPTION OF THE INVENTION

The following Table 1 shows a comparison between the characteristics of the formulation of a masking fluid according to the invention and those of the two products of the prior art above cited.

TABLE 1

Comparison with the masking fluids of the prior art

|  | Formulation of the invention | Healon$^R$ | 1% HPMC |
|---|---|---|---|
| Viscosity (mPa · sec, 10 sec$^{-1}$) | 37 | 6660 | 1030 |
| G'/G" | 0.54 (3 Hz, 37° C.) | 2.67 (1 Hz, 25° C.) | 0.35 (3 Hz, 37° C.) |
| Photoablation speed ($\mu$m/impulse)* | 0.22 | 0.18 | 0.45 |

G' = modulus of elasticity
G" = modulus of viscosity
*Value detected for the corneal tissue: 0.24–0.25 $\mu$m/impulse According to Table 1, the solution of the present invention shows a viscosity lower than that of the Healon$^R$ and a photoablation speed closer to the value of the corneal tissue.

According to a preferred embodiment of the invention, said sodium hyaluronate has a molecular weight from 1,300,000 to 2,000,000 Daltons and a concentration from 0.15% to 0.21% by weight.

In order to enrich the proposed solution with nutritive elements for the corneal tissue improving the tolerability without altering the advantageous characteristics above cited of such solution, and contributing to maintain the isotonicity with the physiologic lachrymal fluid, a formulation according to the invention can comprise also one or more cationic species selected from the group consisting of potassium, calcium and magnesium ion and one or more anionic species selected from the group consisting of chloride, phosphate and citrate and advantageously, glucose. The following minimal concentrations are indicated: 90 mmol/l of sodium ion sodium, 15 mmol/l potassium ion, 0.4 mmol/l of calcium ion, 0.3 mmol/l of magnesium ion, 100 mmol/of chloride ion, 6 mmol/l of phosphate ion, 0.7 mmol/l of citrate and 3 mmol/l of glucose.

In particular, the formulation of masking fluid according to the invention can contain, other than the above indicated values of sodium hyaluronate of defined molecular weight, also the following values of additional elements:

| | | | |
|---|---|---|---|
| Na$^+$ | 90–180 mmol/l | Cl$^-$ | 100–190 mmol/l |
| K$^+$ | 15–30 mmol/l | HPO$_4^-$ | 6–12 mmol/l |
| Ca$^{++}$ | 0.4–0.8 mmol/l | Citrate | 0.7–1.6 mmol/l |
| Mg$^{++}$ | 0.3–0.6 mmol/l | Glucose | 3–7 mmol/l |

According to a further embodiment of the invention the present solution comprises citrate in a quantity of 0.7–2.5 mmol/l. Table 12 shows that in presence of citrate the present solution shows better non-Newtonian properties versus the shear rate.

Because of the optimal properties above shown, the proposed masking fluids give the further advantage to enable an objective evaluation of the evenness of the corneal surface obtained during the surgery, because they enable the intraoperative detection of corneal topography. In fact, differently from the known masking fluids, the formulations according to the invention not only can be rapidly distributed in order to fill the depressed areas of the corneal surface, but also can form, on the whole interested area, a film, which substitutes the epithelium which in its turn has been removed before the treatment, miming exactly its function in respect of the topographic survey.

It is evident that the possibility of performing intraoperative controls of the corneal evenness permits a standardization of the technique of therapeutic photokeratectomy (PTK) and a higher accuracy of the results, with a reduction of the incidence of negative consequences as the induced hypermetropia and the unevenness astigmatism.

FIGS. 11B and 11C show that the use of the solution according to the invention enables to perform a clear topography during the PTK and allows to have a better intraoperative control of the cornea and to evaluate whether to stop the treatment.

The methodology specifically set up for the application of the masking fluid according to the invention develops through the following steps:

Pre-operative Test

Patients underwent to a complete ophthalmologic test and to a corneal topographic test with computerized video keratography (EyeSys Corneal Analysis System, Houston, Tex.). Moreover, detections of corneal pachymetria (that is, of the corneal thickness) were also carried out, both with optical methods (Haag-Streit, Bern, Switzerland) and ultrasonic detectors (Teknar Ophthasonic, St. Louis, Calif.) and, where possible, an endothelial test (Keeler Konan Specular, Japan).

Operative Surgery

An excimer laser is used, at 193 nm Aesculap Meditec Mel 60 with the following parameters: frequency 20 Hz, fluency 250 mJ/cm², slot scanning of 10×2 mm, scanning amplitude 10 mm, scanning speed 5.3 mm/sec.

The scan of the laser slot used covers almost the whole corneal surface, in a way to obtain everywhere a uniform reduction of the corneal thickness.

Before each treatment, the rate of ablation and the homogeneity of the laser beam are checked on photographic paper Agfa L750RC. In case of lack of homogeneity of the laser beam, it is necessary to renew the gas or to remove the technical drawback to determine such homogeneity. As far as fluency, it can be checked by the operator during the whole treatment with the help of two led indicators placed on the laser arm, and possibly it can be modified by intraoperative.

Each patient is submitted to topic anaesthesia with a drop of 0.4% oxybuprocaine and, after application of blepharostat, the corneal epithelium is mechanically removed, with a modified Desmarres paddle. The masking fluid according to the invention is then applied on the cornea and the irradiation can start.

During the treatment, the checking of the frequency of the rolling of masking fluid is carried out by means of fluorescein, which enables to visualize the dried areas, lacking fluid, and also by checking the chromatic-sonic changes that the laser beam assumes when directly hits the corneal tissue and no more the masking fluid. Taking advantage of the characteristic properties of the used masking fluid, during the treatment topographic and ultrasonic pachymetric controls are carried out, to evaluate respectively the real smoothness and evenness of the treated surface and the remaining corneal thickness.

Postoperative Treatment

The postoperative medication requires the administration of a cycloplegic, an antibiotic collyrium and the application of a collagen shield hydrating with a collyrium based on diclofenac. A NSAID with high analgesic properties (ketorolac tromethamine, equal to 12 mg i.m. of morphine) is administered per os every 6 hours for the first 24 hours.

After completion of the reepithelization, a contact lens with therapeutic function (Acuvue, Johnson & Johnson) is applied for the first two months.

Corticosteroids were never administered.

Postoperative Controls

Daily postoperative controls were carried out up to reepithelization and following 1, 2, 3, 6 and 12 months.

Starting from the first month, at each control an ophthalmologic test, including a corneal topography and an endothelioscopy, is carried out.

Further advantages and features of the present invention will be more properly understood in the light of a specific embodiment and of the Figures.

EXAMPLE

Clinical trial with the masking fluids according to the invention and comparison with 2% HPMC solutions The experimentations which follows were performed on the preparation according to the invention, which was named FVA 116 and formulated as follows:

|  | g/100 ml | mmol/l |
| --- | --- | --- |
| sodium hyaluronate | 0.175 | 10 |
| NaCl | 0.684 | 116 |
| KCl | 0.1942 | 26 |
| Na$_2$HPO$_4$.12H$_2$O | 0.3221 | 9 |

-continued

|  | g/100 ml | mmol/l |
| --- | --- | --- |
| Na$_3$ citrate | 0.0308 | 1.2 |
| MgCl$_2$.6H$_2$O | 0.0091 | 0.45 |
| CaCl$_2$.2H$_2$O | 0.0087 | 0.6 |
| glucose | 0.0900 | 5 |

The sodium hyaluronate has a molecular weight comprised from 1,300,000 to 2,000,000 Daltons.

In order to evaluate the performances of such solution compared to a formulation of a masking fluid already largely experimented in PTK by means of excimer laser, an existing marketed solution rendered viscous with 2% by weight hydroxypropylmethylcellulose, which is hereafter indicated as FVC 001, was used.

The clinical trial was carried out on 31 patients suffering of corneal pathologies, which can be treated with therapeutic photokeratectomy, and specifically: Reis-Bueckler's dystrophy (8), Groenouw's palindromia (2), Salzmann's degeneration (1), leukoma (6), post-therapeutic keratitis (2), pterygium (3), corneal foreign body (1), several keratopathies (3), noduli post-keratoplasty (1), corneal erosion (1), alkali burning (2), post-radial keratoplasty and PRK (1).

The patients were divided into two groups: a group of 21, who were treated with FVA 116 and a group of 10, who were treated with FVC 001. The methodology of excimer laser photokeratectomy applied to the two groups is that previously described, with the only variable element consisting in the use of one or the other of the two masking fluids (FVA 116 and FVC 001). Clearly, in consequence of such single difference, it was not possible to perform the intraoperative topographic controls on the group of patients treated with the masking fluid based on methylcellulose, and the corneal topography was detected only after the surgery, at the end of the reepithelization process.

The results of the PTK treatment were verified by means of controls before and after the treatment, according to the methodology already described. In particular, as it will be described more in detail, in all the patients were evaluated:

natural and regulated vision acuity before the laser treatment and every month up to 12 months;

equal-sphere, sphere and cylinder before and after the laser treatment and every month up to 12 months;

haze before the laser treatment and every month up to 12 months.

As it is known, the vision acuity is the capacity to understand and distinguish the spatial details, and it gives a measure of the smaller retinal image, the form of which can be recognized. With or without pathologies of the ophthalmencephalon the vision acuity is conditioned by the presence of refractive errors, therefore its measurement must necessary be preceded by a refraction test by objective methods (skiascopy, ophthalmetria, etc.) and with subjective methods (Donders method). After such test, the natural or not-regulated vision and the regulated vision, more interesting for its clinical aspects, can then be detected with conventional methods.

Figure 1:
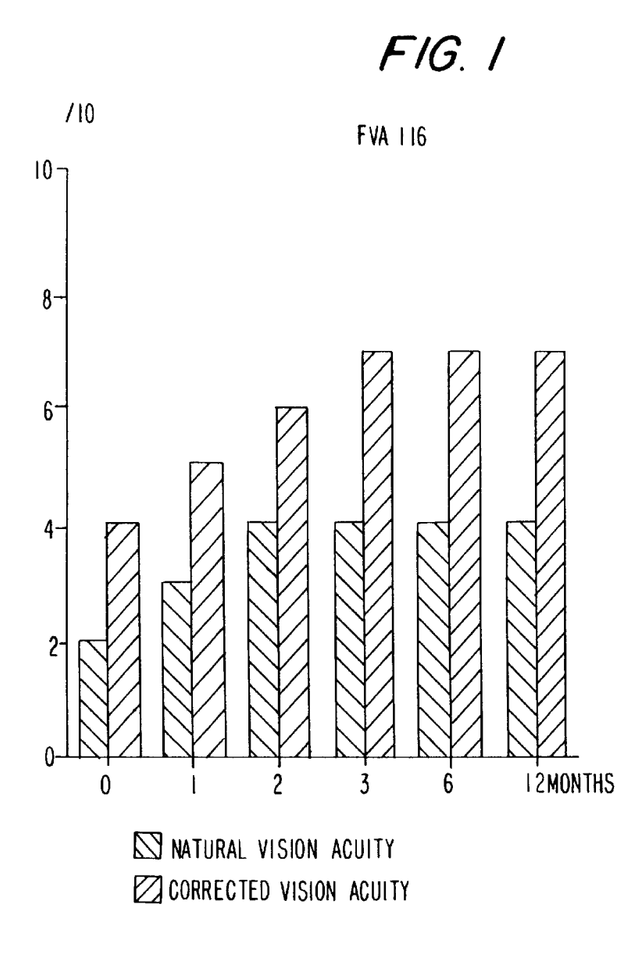
FIGS. 1 and 2 show the detected values of the vision acuity, natural and regulated, before and after the PTK treatment for two different groups of patients, treated with the product according to the invention and a product of the prior art respectively as masking fluid.
Figure 2:
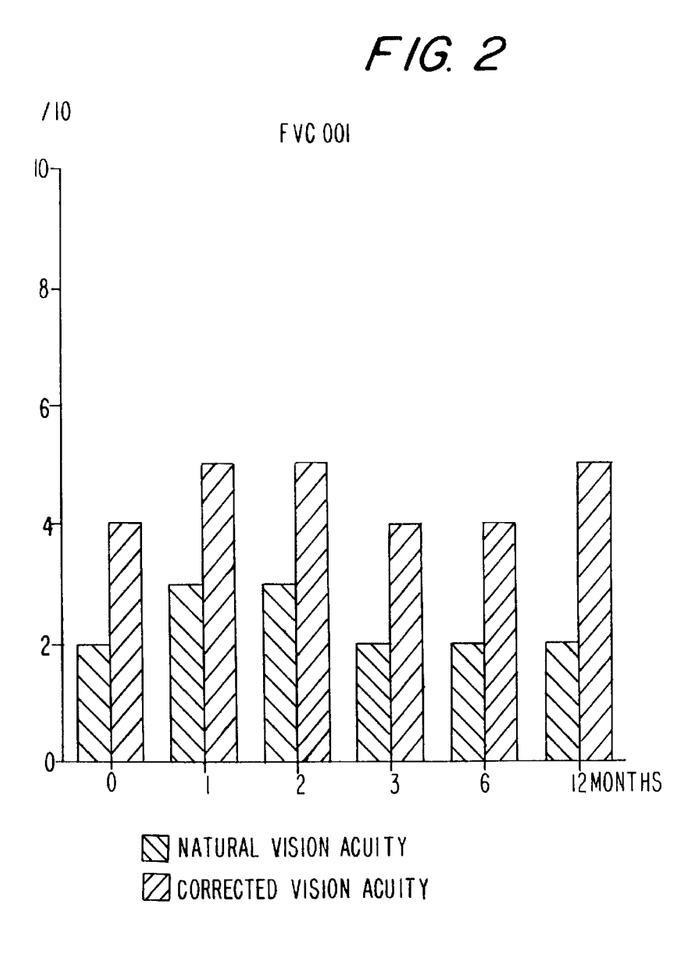
Figure 3:
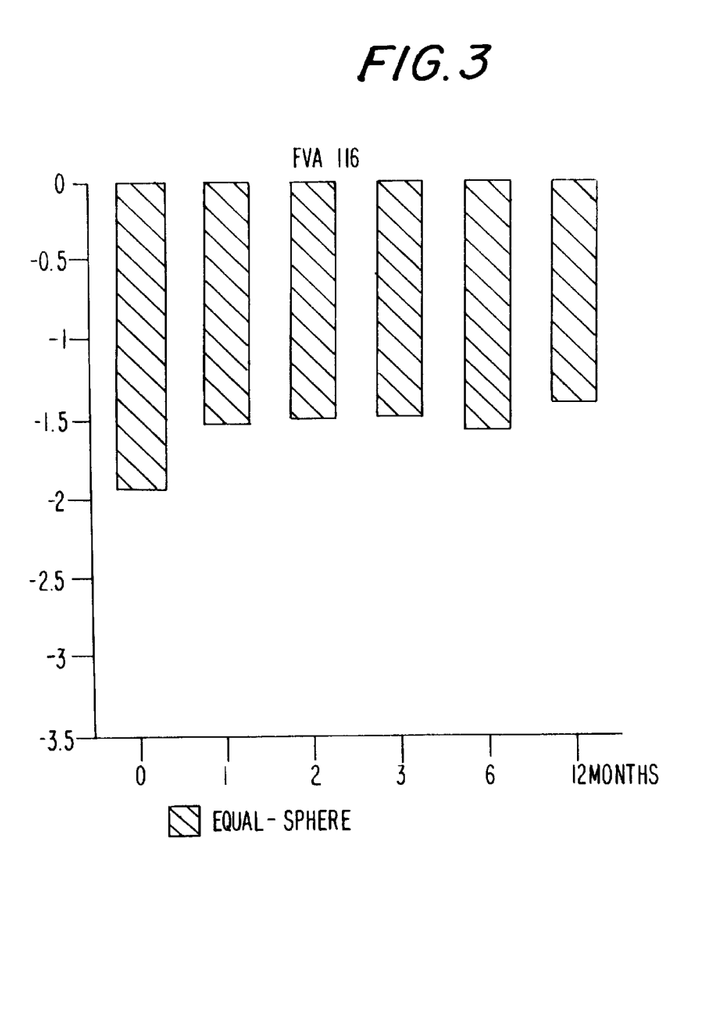
FIGS. 3 and 4 show the detected values of the equalsphere before and after the PTK treatment for the same two groups of patients relative to FIG. 1 and 2, respectively.
Figure 4:
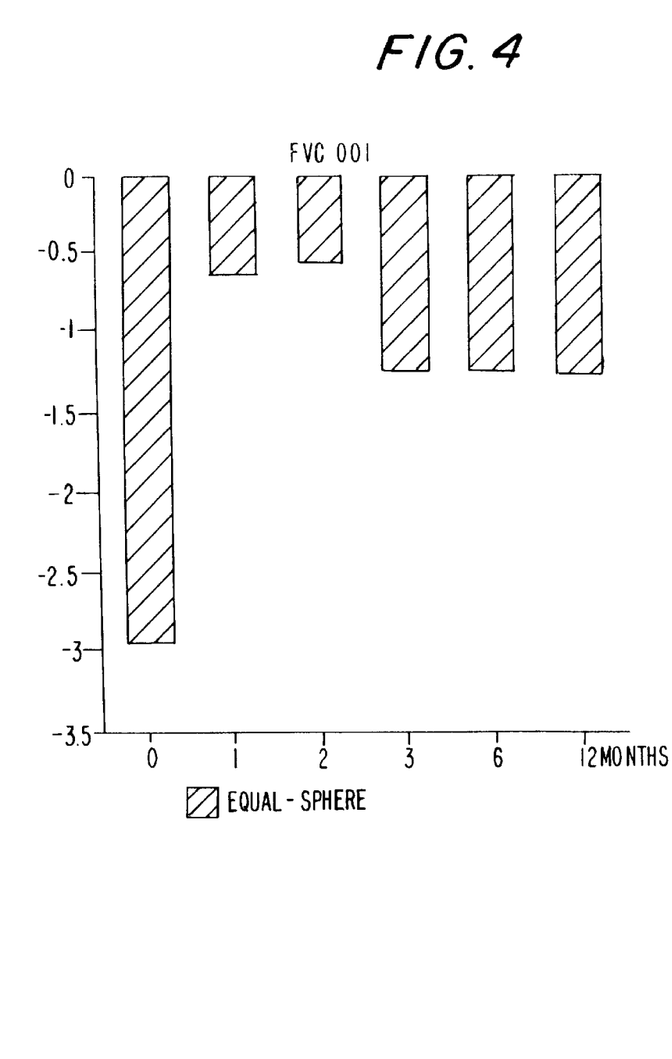
Figure 5:
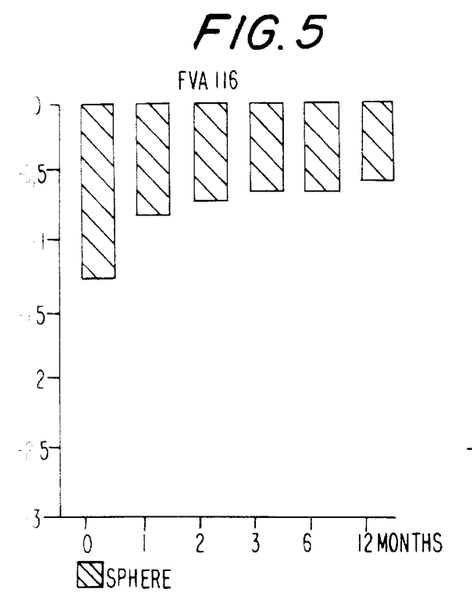
FIGS. 5 and 6 show the detected values of the sphere before and after the PTK treatment for the same two groups of patients.
Figure 6:
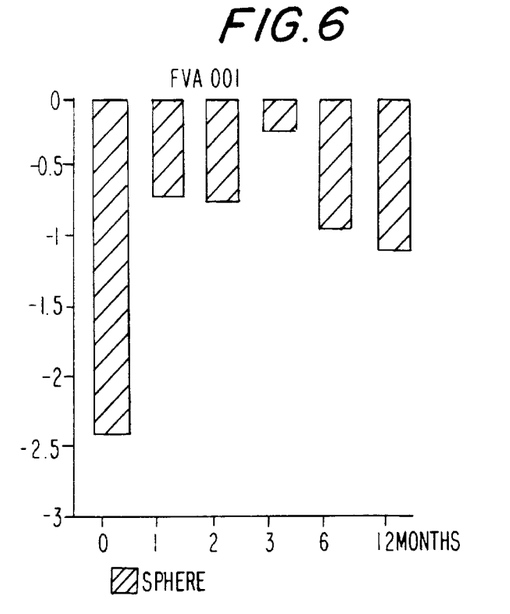
Figure 7:
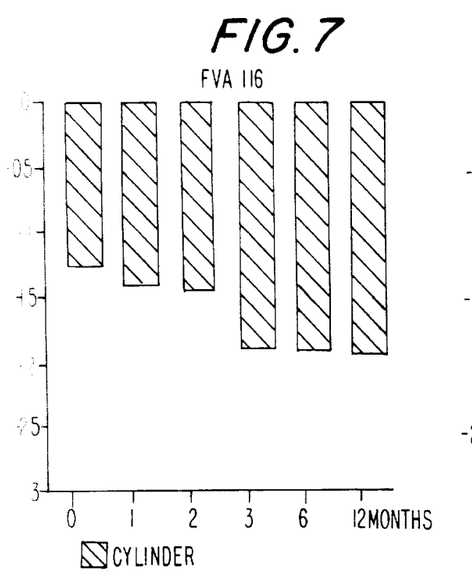
FIGS. 7 and 8 show the same detected values of the cylinder before and after the PTK treatment for the same two groups of patients.
Figure 8:
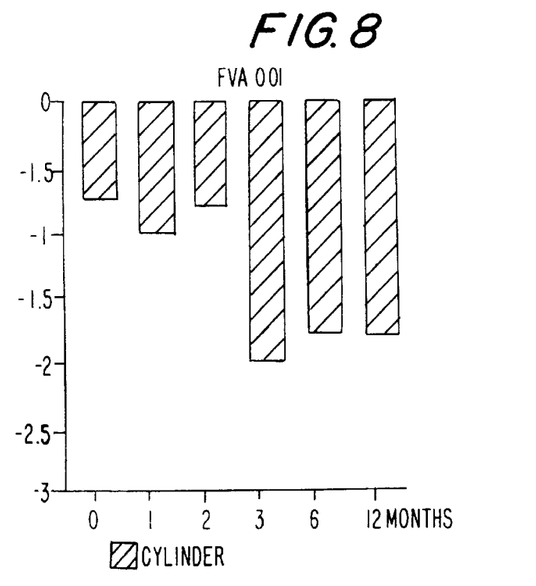

The results of vision acuity tests, natural and regulated, before the operation (time 0) and at 1, 2, 3, 6 and 12 months, referred both to the group of patients operated using the masking fluid of the invention and to the group, who was operated using the HPMC solution, are reported in the following Table 2, and in the histograms of FIGS. 1 and 2, respectively.

TABLE 2

VISION ACUITY TESTS

| Time | Natural vision acuity (/10) | | Corrected vision acuity (/10) | |
|---|---|---|---|---|
| (Months) | FVA 116 | FVC 001 | FVA 116 | FVC 001 |
| 0 | 2 | 2 | 4 | 4 |
| 1 | 3 | 3 | 5 | 5 |
| 2 | 4 | 3 | 6 | 5 |
| 3 | 4 | 2 | 7 | 4 |
| 6 | 4 | 2 | 7 | 4 |
| 12 | 4 | 2 | 7 | 5 |

The data previously reported show that, both natural and corrected vision acuity of patients, who were treated with the masking fluid based on sodium hyaluronate according to the invention are improved if compared to the basal value, in a way statistically significant (Student's t-test) at all the considered times. On the contrary, patients treated with FVC 001 as masking fluid show a natural vision acuity which, after a first improvement, goes back to the basal value within three months after the operation, whilst that corrected is lightly improved in the first two months of the treatment, then goes back to the basal value and lightly improves again one year after the treatment.

Further fundamental data for a right study of the results of the therapeutic photokeratectomy relate to the evaluation of the corneal curvature, which is essential in many clinical situations to determine the simple astigmatic refraction or irregular refraction. As already shown, one of the critical aspects of PTK is the induction of astigmatism and hypertropia in consequence of an unhomogeneous photoablation.

Therefore, in all the treated patients, the values of the equal-sphere, sphere and cylinder were detected. Such values, both for the group of patients treated with the masking fluid according to the invention and the control group with the fluid of the state of the art, were reported in the following Table 3, and they are graphically expressed in FIGS. from 3 to 8.

TABLE 3

EVALUATION OF THE CORNEAL CURVATURE

| Time | Equal-sphere (Diopters) | | Sphere (Diopters) | | Cylinder (Diopters) | |
|---|---|---|---|---|---|---|
| (Months) | FVA 116 | FVC 001 | FVA 116 | FVC 001 | FVA 116 | FVC 001 |
| 0 | −1.91 | −2.92 | −1.27 | −2.41 | −1.26 | −0.75 |
| 1 | −1.51 | −0.61 | −0.81 | −0.71 | −1.42 | −1.01 |
| 2 | −1.49 | −0.55 | −0.71 | −0.75 | −1.45 | −0.81 |
| 3 | −1.47 | −1.22 | −0.64 | −0.25 | −1.89 | −2.01 |
| 6 | −1.55 | −1.24 | −0.65 | −0.97 | −1.92 | −1.81 |
| 12 | −1.39 | −1.25 | −0.54 | −1.11 | −1.95 | −1.83 |

The values of equal-sphere, sphere and cylinder, above reported, show that the use of the masking fluid FVA 116 implies a remarkable reduction of negative effects on the sphere and cylinder compared to HPMC, also if such effects are entirely eliminated. It is therefore evident the advantage of the use of a suitable masking fluid and of the intra-treatment topographic check in order to reduce the effect of hypermetropia, which results increased by an unhomogeneous ablation.

Fundamental for the ascertainment of the results following to the use of PTK is the verification of the haze, practically consisting of rendering opaque the corneal epithelium or stroma which is usually present in patients subjected to therapeutic photokeratectomy.

Figure 9:
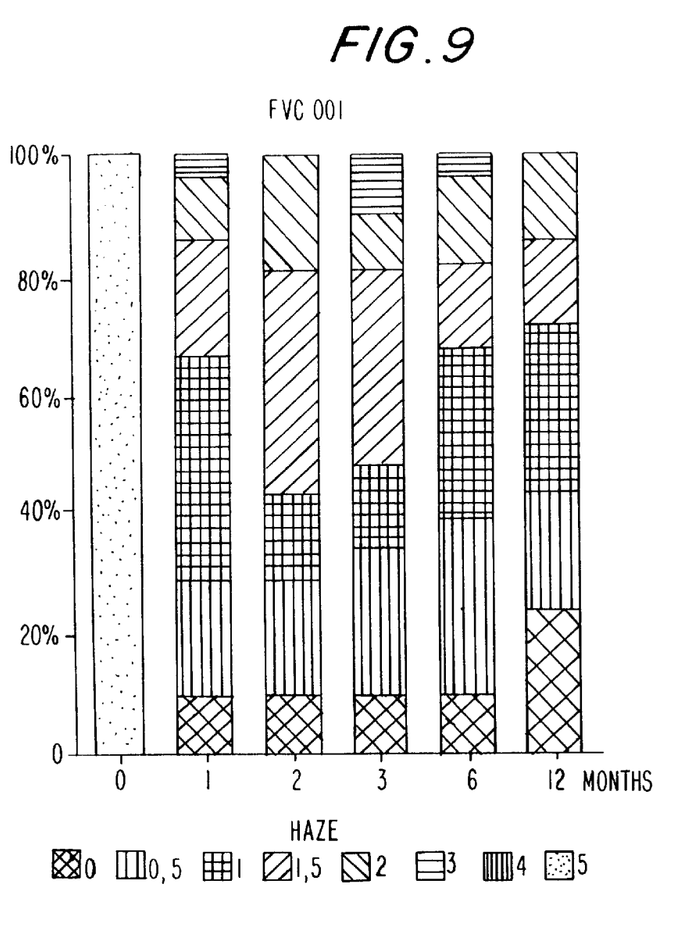
FIGS. 9 and 10 show the detected values of the haze before and after the PTK treatment for the same two groups of patients.
Figure 10:
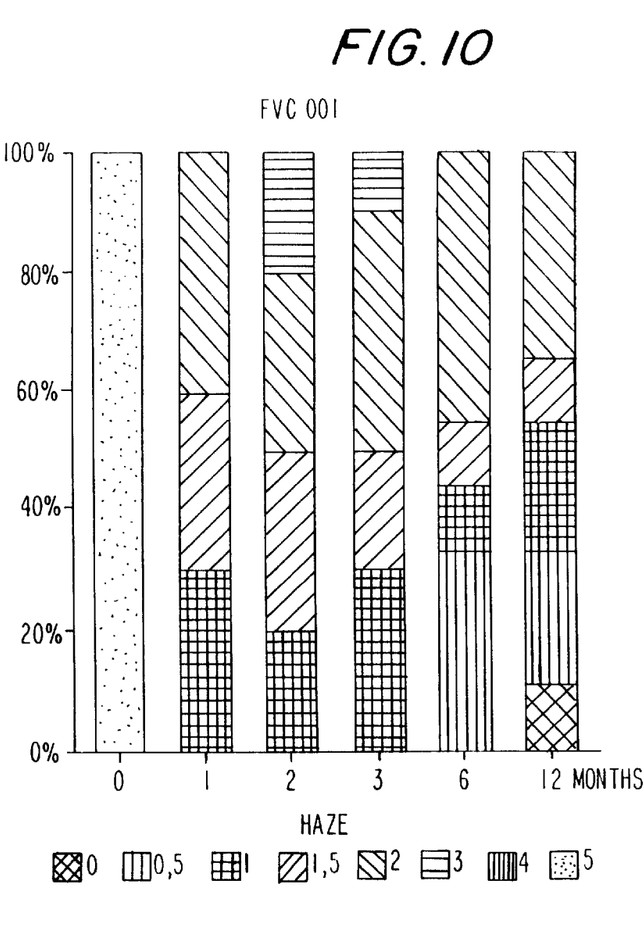

In the study herein reported, the quantification of the degree of corneal opacity was performed giving values according to the following scale:

H=0 totally transparent cornea;
H=0.5 slight opacity visible only with a tangential indirect illumination;
H=1 visible minimal veiling in slot at different angles;
H=2 opacity of thickness comparable to the epithelium, easily visible at direct illumination with slot;
H=3 opacity of moderate density, good visibility at direct light, which reduces slightly the iris details;
H=4 opacity of accentuated density, visible at room light, which darkens the iris details;
H=6 opacity which prevents the camera anterior test;

The following Tables 4 and 5 and the corresponding FIGS. 9 and 10 report the values for haze detected in the two groups of patients before and after the treatment, measured according to the previous scale.

TABLE 4

CORNEAL OPACITY (HAZE) TEST
Patients treated with FVA 116

| Time | Percentage with value | | | | | | | |
|---|---|---|---|---|---|---|---|---|
| (Months) | 5 | 4 | 3 | 2 | 1.5 | 1 | 0.5 | 0 |
| 0 | 100 | — | — | — | — | — | — | — |
| 1 | — | — | 4 | 10 | 19 | 38 | 19 | 10 |
| 2 | — | — | — | 19 | 38 | 14 | 19 | 10 |
| 3 | — | — | 10 | 9 | 33 | 14 | 24 | 10 |
| 6 | — | — | 4 | 14 | 14 | 19 | 29 | 10 |
| 12 | — | — | — | 14 | 14 | 29 | 19 | 24 |

TABLE 5

CORNEAL OPACITY (HAZE) TEST
Patients treated with FVC 001

| Time | Percentage with value | | | | | | | |
|---|---|---|---|---|---|---|---|---|
| (Months) | 5 | 4 | 3 | 2 | 1.5 | 1 | 0.5 | 0 |
| 0 | 100 | — | — | — | — | — | — | — |
| 1 | — | — | — | 40 | 30 | 30 | — | — |
| 2 | — | — | 20 | 30 | 30 | 20 | — | — |
| 3 | — | — | 10 | 40 | 20 | 30 | — | — |
| 6 | — | — | — | 45 | 11 | 11 | 33 | — |
| 12 | — | — | — | 34 | 11 | 22 | 22 | 11 |

From the data shown above, it is evident that the decreasing of the corneal opacity compared to the basal value is more relevant and more rapid in those patients treated with the masking fluid of the invention than in those treated with HPMC.

In particular, in the cases treated with FVA 116, as masking fluid, it was detected at 12 months an opacity degree from 0 to 1 (from total transparency to slight opacity) in 72% of patients and from 1.5 to 2 (from slight opacity to thickness opacity comparable to the epithelium) in 28% of the patients, whilst in the cases treated with FVC 001, as masking fluid, it was detected an opacity degree at 12 months from 0 to 1 in 55% of patients and from 1.5 to 2 in 45% of cases. Moreover, the opacity reduction was more rapid in patients treated with the masking fluid of the invention.

Further, the present invention relates to a therapeutic photokeratectomy method for the treatment of the cornea by means of an excimer laser comprising the introduction in the eye, as masking fluid, of a formulation in sodium hyaluronate viscous aqueous solution, wherein said sodium hyaluronate has a molecular weight comprised from 1,200,000 to 2,200,000 Daltons, preferably from 1,300,000 to 2,000,000 Daltons, a concentration from 0.10% to 0.40% by weight, preferably from 0.15% to 21%, and a viscosity from 30 to 43 mPa.sec at 10 sec$^{-1}$, preferably 37 mPa.sec at 10 sec$^{-1}$.

I claim:

1. A viscous aqueous formulation, useful as a masking fluid for therapeutic photokeratectomy by means of excimer laser, comprising sodium hyaluronate having a molecular weight ranging from 1,200,000 to 2,200,000 Daltons, at a concentration ranging from 0.10% to 0.40% by weight, and having a viscosity ranging from 30 to 43 mPa.sec at 10 sec-1, said formulation optionally comprising one or more cation species selected from the group consisting of sodium, potassium, calcium and magnesium ions and/or one or more anion species selected from the group consisting of chloride, phosphate and citrate ions.

2. The formulation according to claim 1, comprising citrate at the concentration of 0.7–1.6 mmol/l.

3. The formulation according to claim 2, also comprising glucose.

4. The formulation according to claim 3, comprising the following minimal amounts of ionic species: 90 mmol/l sodium ion, 15 mmol/l potassium ion, 0.4 mmol/l calcium ion, 0.3 mmol/l magnesium ion, 100 mmol/l chloride ion, 6 mmol/l phosphate ion, 0.7 mmol/l citrate ion, and at least 3 mmol/l glucose.

5. The formulation according to claim 4, comprising the following species at the following concentrations:

| Na$^+$ | 90–180 mmol/l | Cl$^-$ | 100–190 mmol/l |
| K$^+$ | 15–30 mmol/l | HPO$_4^=$ | 6–12 mmol/l |
| Ca$^{++}$ | 0.4–0.8 mmol/l | Citrate | 0.7–1.6 mmol/l |
| Mg$^{++}$ | 0.3–0.6 mmol/l | Glucose | 3–7 mmol/l |

6. The formulation according to claim 5 comprising:

|  | g/100 ml | mmol/l |
| --- | --- | --- |
| sodium hyaluronate | 0.175 | 10 |
| NaCl | 0.684 | 116 |
| KCl | 0.1942 | 26 |
| Na$_2$HPO$_4$.12H$_2$O | 0.3221 | 9 |
| Na$_3$ citrate | 0.0308 | 1.2 |
| MgCl$_2$.6H$_2$O | 0.0091 | 0.45 |
| CaCl$_2$.2H$_2$O | 0.0087 | 0.6 |
| glucose | 0.0900 | 5 | and wherein the sodium hyaluronate has a molecular weight from 1,300,000 to 2,000,000 Daltons.

7. A therapeutic photokeratectomy method for the treatment of the cornea by means of an excimer laser comprising the following steps:

1) introducing in the eye, as masking fluid, a suitable amount of a viscous aqueous formulation containing sodium hyaluronate having a molecular weight ranging from 1,200,000 to 2,200,000 Daltons, at a concentration ranging from 0.10% to 0.40% by weight, said formulation having a viscosity ranging from 30 to 43 mPa.sec at 10 sec-1; and 2) ablating corneal or macula unevenness by applying excimer laser pulses at 193 nm.

8. The method according to claim 7, wherein said sodium hyaluronate has a molecular weight ranging from 1,300,000 to 2,000,000 Daltons, at a concentration of 0.15% to 0.21% by weight, and said viscous aqueous formulation has a viscosity of 37 mPa.sec at 10 sec-1.

9. The method according to claim 7, wherein said aqueous formulation also comprises one or more cationic species selected from the group consisting of sodium, potassium, calcium and magnesium ions and/or one or more anionic species selected from the group consisting of chloride, phosphate and citrate ions.

10. The method according to claim 9, wherein said formulation comprises citrate at the concentration of 0.7–1.6 mmol/l.

11. The method according to claim 9, wherein said formulation also comprises glucose.

12. The method according claim 11, wherein said formulation comprises the following minimal amounts of ionic species: 90 mmol/l sodium ion, 15 mmol/l potassium ion, 0.4 mmol/l calcium ion, 0.3 mmol/l magnesium ion, 100 mmol/l chloride ion, 6 mmol/l phosphate ion, 0.7 mmol/l citrate ion, and at least 3 mmol/l glucose.

13. The method according to claim 12, wherein said formulation comprises the following species at the following concentrations:

| Na$^+$ | 90–180 mmol/l | Cl$^-$ | 100–190 mmol/l |
| K$^+$ | 15–30 mmol/l | HPO$_4^=$ | 6–12 mmol/l |
| Ca$^{++}$ | 0.4–0.8 mmol/l | Citrate | 0.7–1.6 mmol/l |
| Mg$^{++}$ | 0.3–0.6 mmol/l | Glucose | 3–7 mmol/l |

14. The method according to claim 7 and including the further step of keratoscopically controlling the corneal topography during photoablation to evaluate the effects on the corneal surface.

* * * * *